(12) United States Patent
Ader

(10) Patent No.: US 6,973,374 B2
(45) Date of Patent: Dec. 6, 2005

(54) METHOD AND DEVICE FOR ADMINISTERING MEDICATION AND/OR PLACEBO

(75) Inventor: Robert Ader, Pittsford, NY (US)

(73) Assignee: University of Rochester, Rochester, NY (US)

( * ) Notice: Subject to any disclaimer, the term of this patent is extended or adjusted under 35 U.S.C. 154(b) by 109 days.

(21) Appl. No.: 10/450,879

(22) PCT Filed: Dec. 19, 2001

(86) PCT No.: PCT/US01/49296

§ 371 (c)(1),
(2), (4) Date: Nov. 3, 2003

(87) PCT Pub. No.: WO02/49503

PCT Pub. Date: Jun. 27, 2002

(65) Prior Publication Data

US 2004/0153214 A1 Aug. 5, 2004

Related U.S. Application Data

(60) Provisional application No. 60/256,633, filed on Dec. 19, 2000.

(51) Int. Cl.[7] .......................... A61M 5/00; G05D 7/00
(52) U.S. Cl. ................ 700/282; 700/281; 604/186; 604/246; 604/500
(58) Field of Search ........................... 700/281, 282; 604/90.01, 131, 186, 207, 246, 500

(56) References Cited

U.S. PATENT DOCUMENTS

| | | | |
|---|---|---|---|
| 4,778,449 A * | 10/1988 | Weber et al. ............... | 604/65 |
| 4,925,444 A | 5/1990 | Orkin et al. | |
| 5,171,214 A | 12/1992 | Kolber et al. | |
| 5,207,642 A | 5/1993 | Orkin et al. | |
| 5,368,562 A | 11/1994 | Blomquist et al. | |
| 5,378,126 A | 1/1995 | Abrahamson et al. | |
| 5,378,231 A | 1/1995 | Johnson et al. | |
| 5,431,627 A | 7/1995 | Pastrone et al. | |
| 5,466,227 A | 11/1995 | Kessenich | |
| 5,485,408 A | 1/1996 | Blomquist | |
| 5,496,273 A | 3/1996 | Pastrone et al. | |
| 5,522,798 A | 6/1996 | Johnson et al. | |
| 5,547,470 A | 8/1996 | Johnson et al. | |
| 5,685,844 A | 11/1997 | Marttila | |
| 5,718,562 A | 2/1998 | Lawless et al. | |
| 5,745,378 A | 4/1998 | Barker et al. | |
| 6,053,887 A * | 4/2000 | Levitas et al. ............... | 604/500 |
| 6,092,660 A | 7/2000 | Rune et al. | |

OTHER PUBLICATIONS

Ader, *Psychoneuroimmunology* pp. 669-696.
Ader, *Mediational Theory* pp. 306-323.
Ader, in *The Placeb: An interdisciplinary Exploration* harrington, A. (Ed.), Harvard University Press: Cambridge.

(Continued)

Primary Examiner—Jayprakash N. Gandhi
(74) Attorney, Agent, or Firm—Nixon Peabody LLP

(57) ABSTRACT

A control device and a drug delivery system containing such a control device are disclosed for delivery to a patient of a drug or a placebo (or ineffective dose of the drug) according to a partial reinforcement schedule, whereby the placebo (or ineffective dose of the drug) is delivered in whole or in part during one or more delivery events. Methods of modulating the drug/placebo delivery to a patient are also provided, whereby the delivery event is initiated either according to a patient-initiated signaling event (i.e., a self-medication mode) or an automated signaling event (i.e., automated mode).

20 Claims, 2 Drawing Sheets

OTHER PUBLICATIONS

Olness et al., *Developmental and Behavioral Pediatrics* 13(2):124-125 (1992).
Giang et al., *Journal of Neuropsychiatry* 8(2):194-201 (1996).
Suchman et al., *Clin Pharmacol Ther* 52(4):372-377 (1992).
Ader et al., *Science* 215:1534-1536 (1982).
Ader, *Psychological Medicine* 23:297-299 (1993).
Ader, *Arthritis Care Res.* 2(3):S58-S64 (1989).
Ader, *Integr Psychiatry* 6:165-170 (1989).
Ader, In *Experimental Foundations of Behavioral Medicine: Conditioning Approaches*, Ader et al. (Eds.) pp. 47-66 (1988).

* cited by examiner

METHOD AND DEVICE FOR ADMINISTERING MEDICATION AND/OR PLACEBO

This application claims the priority benefit of U.S. Provisional Patent Application Ser. No. 60/256,633, filed Dec. 19, 2000, which is hereby incorporated by reference in its entirety.

FIELD OF THE INVENTION

The present invention relates generally to a method for administering a drug bolus or placebo bolus, or both, to a patient, either automatically or by patient control, as well as a drug infusion system which is adapted for practicing such method.

BACKGROUND OF THE INVENTION

At a descriptive level, the response to inert or therapeutically irrelevant substances or placebos can be viewed as a conditioned response. Conditioning, however, remains one of the primary but least studied analyses of the "placebo effect". In behavioral terms, the physiological (and therapeutic) effects unconditionally elicited by drugs are unconditioned responses. Thus, the drug itself can be considered an unconditioned stimulus. Environmental or behavioral events or stimuli that are neutral with respect to the unconditioned administration of drug, including the pill or injection itself, can be considered conditioned stimuli. Thus, the response to an inert (or therapeutically irrelevant) substance or placebo has been described as a conditioned response. Several investigators have hypothesized that the entire ritual associated with drug administration can take on the properties of a conditioned stimulus by virtue of repeated association of these neutral events with the unconditioned effects of drug administration in the history of the patients (see, e.g., Wickrameskera, "A Conditioned Response Model of the Placebo effect: Predictions from the Model," *Biofeedback and Self Regulation* 5:5–18 (1980); White et al. (eds.), *Placebo: Theory, Research and Mechanisms,* Guilford: New York, N.Y. (1985); Gadow & Poling (eds.), *Methodological Issues in Human Psychopharmacology: Advances in Learning and Behavioral Disabilities* (Suppl. 1), JAI Press: Greenwich, Conn. (1986); Ader, "The Placebo Effect is a Conditioned Stimulus," *In Experimental Foundations of Behavioral Medicine: Conditions Approaches,* (Ader et al., eds.), pp. 47–66, Lawrence Erlbaum: Hillsdale, N.J. (1988)).

Most drug studies involve an experimental group which receives an active drug whenever medication is administered. This is a continuous or 100 percent reinforcement schedule (i.e., stimulus is invariably associated with drug administration, which reinforces the association of the stimulus with the unconditioned effects of the drug). A control or placebo group receives no active drug whatsoever (i.e., stimulus is never associated with drug effects, providing absolutely no reinforcement, a zero percent reinforcement schedule). While the concept of partial reinforcement schedules in pharmacotherapy has been identified (see Ader, "The Role of Conditioning in Pharmacotherapy," *In The Placebo Effect: An Interdisciplinary Exploration,* Harrington (ed.), pp. 138–165, Harvard Univ. Press, Cambridge, Mass. (1997)), applicant believes that there exists a need for a device which is capable of carrying out partial reinforcement schedules, i.e., schedules of reinforcement between zero percent and 100 percent.

In recent years, microprocessor controlled drug infusion systems have become relatively common. A typical control for a drug delivery system includes a keypad or other user interface enabling a medical practitioner to enter the rate of drug delivery, duration, and volume of a drug or medicinal fluid, quite often analgesic agents, to be infused into a patient.

Drug delivery is normally either programmed to occur as a continuous infusion or single or multiple bolus doses over a course of time, or via self-administration. Each drug delivery mode offers its own benefits and drawbacks. From a clinical perspective, patients capable of self-administering feel that they are in greater control over their situation. (As a result, most patients self-medicate themselves less frequently than an automated program would require.) Regardless of the administration mode, however, such drug infusion systems offer only continuous reinforcement since they are equipped to administer the drug alone all the time.

While drug infusion systems have been described for the delivery of multiple drugs as well as hydrating fluid, such devices have previously been unable to effect a partial reinforcement schedule of drug delivery, by administering both drug and placebo.

The present invention is directed to overcoming this and other deficiencies in the art.

SUMMARY OF THE INVENTION

A first aspect of the present invention relates to a control device for a drug delivery system equipped to deliver at least two fluids, an effective dose of a drug in fluid form and either a placebo or an ineffective dose of the drug in fluid form, the control device including: a processor that is controlled in accordance with a set of program instructions that determine a partial reinforcement schedule for drug administration; a memory, coupled to the processor, said memory storing the set of program instructions and a set of parameters for the partial reinforcement schedule; and a user interface, coupled to the processor, said user interface enabling a user to input at least some of the set of parameters used by the partial reinforcement schedule; wherein the processor, in executing the set of program instructions, delivers the effective dose of the drug, the placebo or ineffective dose of the drug, or both, to a patient according to the partial reinforcement schedule.

A second aspect of the present invention relates to a drug delivery system which includes: a housing; a first receptacle in said housing which is adapted to receive a first container including an effective dose of a drug in fluid form; a second receptacle in said housing which is adapted to receive a second container including a placebo or an ineffective dose of the drug in fluid form; an outlet which, upon introduction of the first and second containers into the first and second receptacles, respectively, is in communication therewith; one or more pumps which act upon the first and second containers; and a control device which controls operation of the one or more pumps to deliver the effective dose of the drug or the placebo or ineffective dose of the drug from the outlet according to a partial reinforcement schedule, whereby the placebo or ineffective dose of the drug is delivered in whole or in part during one or more delivery events.

A third aspect of the present invention relates to a method of automatically modulating drug/placebo delivery to a patient which includes: connecting a fluid supply line of a patient to an outlet of a drug delivery system of the present invention, with the drug delivery system provided with a first container including an effective dose of a drug in fluid form and a second container including either a placebo or an ineffective dose of the drug in fluid form; programming the control device with a drug dosage rate for a predetermined period of time; and operating the drug delivery system for the predetermined period of time, whereby drug delivery during the predetermined period of time is modulated by delivery of the placebo or the ineffective dose of the drug, either in whole or in part, during one or more delivery events occurring during the predetermined period of time.

A fourth aspect of the present invention relates to a method of modulating patient self-delivery of a drug which includes: connecting a fluid supply line of a patient to an outlet of a drug delivery system of the present invention, with the drug delivery system provided with a first container including an effective dose of a drug in fluid form and a second container including a placebo or an ineffective dose of the drug in fluid form; programming the control device with a drug dosage rate; and operating the drug delivery system, whereby drug delivery is modulated by delivery of the placebo or the ineffective dose of the drug, either in whole or in part, during one or more patient-regulated delivery events.

The present invention offers a number of advantages. By capitalizing on conditioning which is an inherent component of drug therapy regimes, the prescription of partial schedules of pharmacotherapeutic reinforcement will allow a reduction in the total amount of drug required to treat some pathophysiological condition or maintain some physiologic state within homeostatic limits. Under conditions where a clinician might want to increase the dose of medication but is constrained by toxic target organ effects, an ostensible increase in the amount of drug being taken can be achieved by holding dose constant but using conditioned stimuli to increase the number of occasions when medication apparently is administered. A modified partial pharmacotherapeutic reinforcement can capitalize on the ability of a conditioned stimulus (e.g., sound of drug delivery system, lights on the drug delivery system, or tactile sensation accompanying fluid delivery) to potentiate the effects of a low, ineffective, or minimally effective dose of an active drug. From the perspective of overall patient health, a partial pharmacotherapeutic reinforcement can reduce the magnitude of side effects because conditioned responses are not typically as large as unconditioned responses. (If side effects are reduced, then adherence to the treatment protocol can be enhanced, providing greater therapeutic efficacy.) Moreover, partial pharmacotherapeutic reinforcement should extend the effects of pharmacotherapy by increasing patient resistance to experimental extinction. Continued presentation of conditioned stimuli after cessation of drug administration would extend the effects of active drug administration for a longer period of time as compared to patients that did not continue to receive conditioned stimuli and patients that had received a continuous schedule of pharmacologic reinforcement.

DETAILED DESCRIPTION OF THE INVENTION

The present invention relates generally to a control device for a drug delivery system which is equipped for delivery of multiple fluids from multiple fluid sources, either according to an automated mode or according to a self-administration mode. Specifically, the control device is capable of executing delivery of a drug according to a partial reinforcement schedule whereby a placebo or ineffective dose of the drug is provided to a patient, either in whole or in part, during one or more drug delivery events carried out according to a set of program instructions.

As used herein, the term "partial reinforcement schedule" is intended to mean reinforcement of a conditioned stimulus with an unconditioned stimulus between zero and 100 percent of the time in which a conditioned stimulus occurs. In this case, a conditioned stimulus occurs as a delivery event executed by the drug delivery system. The actual conditioned stimulus can take the form of audible, visual, and/or tactile stimuli which occur as the drug delivery system delivers a fluid to a patient. Thus, a partial reinforcement schedule provides a patient with less reinforcement than a continuous or 100 percent reinforcement schedule provides, but more reinforcement than an non-reinforced (or placebo) schedule provides.

While the control device and drug delivery system are intended to be used to administer a partial reinforcement schedule, they are also capable of being used to deliver a continuous or 100 percent reinforcement schedule as well as a non-reinforced or zero percent reinforcement schedule. This is beneficial to care providers, who need not supply two separate drug delivery systems, one for continuous reinforcement and a drug delivery system according to the present invention for partial reinforcement.

By placebo delivery, either in whole or in part, it is intended that the control device (and, therefore, the drug delivery system as well) be capable of delivering no active drug whatsoever during a delivery event (wholly placebo) as well as an effective partial or sub-maximal dosage of active drug during a delivery event.

As an alternative to use of a placebo, an ineffective dose of the same active drug can be administered to the patient. By ineffective dose, it is intended that the quantity of drug administered during a delivery event is so low that it practically cannot yield an unconditioned response which occurs following delivery of a maximum dose of the active drug or an effective sub-maximal dose of the active drug. Use of an ineffective dose of the active drug would allow a patient to receive some drug all of the time (as opposed to no drug some of the time).

The drug delivery system of the present invention can be prepared by adapting the control device of a pre-existing multi-channel drug delivery system or by preparing the drug delivery system from component parts as discussed below.

Figure 1:
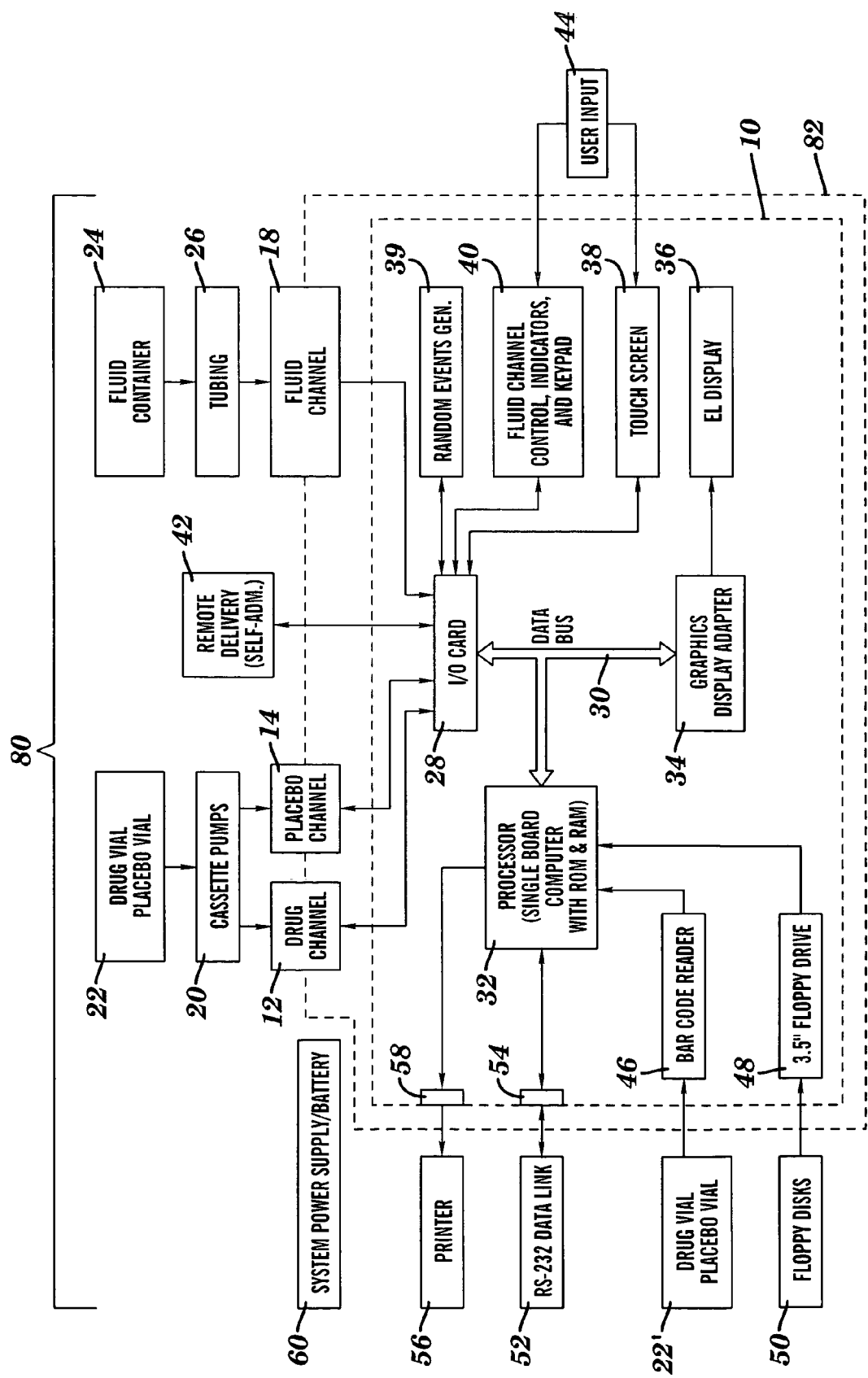
FIG. 1 is a schematic diagram illustrating a drug delivery system according to the present invention, which includes a control device of the present invention.

With reference to FIG. 1, the components of a control device 10 are disclosed, in connection with a multi-channel drug delivery system 80 that includes two "channels", a "drug channel" 12 and a "placebo channel" 14, as well as a separate "fluid channel" 18. For purposes of this disclosure, a "channel" refers to an independent path through which a drug in fluid form, placebo in fluid form, or other typical fluid (e.g., a hydrating fluid) is delivered to a patient from a source container, either through a separate line or to a manifold, from which one or more drugs are infused into the patient. The drug and placebo are separately input to the manifold through one-way check valves and then flow through a common line to the patient from an outlet of the manifold. Thus, each channel may include a separate outlet or a single outlet can be provided for each. The term "fluid channel," as used herein, refers to a path through which a fluid is delivered to the manifold from a source and then to the patient. The patient typically receives the drug or placebo intravenously, but other types of drug infusion are also contemplated.

In one embodiment, control device 10 is integrally contained within housing 82 of the multi-channel drug delivery system and is linked thereto by a plurality of electrical paths. Although control device 10 can readily be adapted for controlling other types of multi-channel drug delivery systems, in the embodiment discussed below it controls two or more cassette pumps 20 that dispense the drug or placebo to the patient in a liquid form. Fluid channel 18 is used for administering a hydration liquid and/or for flushing the manifold and the common line that delivers the drugs to the patient from the manifold.

The drug delivery system shown in FIG. 1 accepts separate drug or placebo vials 22 as the source of the drug or placebo which is administered through the drug channel or placebo channel, respectively. Pump cassettes 20 are of conventional design (e.g., pump cassettes available from Abbott Laboratories for use in its LifeCare™ systems) and a received within a receptacle of the housing 82. (As shown in the figures, pump cassettes 20 are intended to designate both the cassette and the receptacle within housing 82.) The pump cassettes typically comprise a plastic housing with passages, valves, and chambers through which liquid flows as a piston displaces an elastomeric membrane accessed through a pumping port formed in the cassette housing. Each of the channels 12, 14 is able to deliver liquid drug or placebo to a patient at a rate in the range from about 0.1 ml to about 1200 ml per hour; however, pumps having substantially different delivery rates can also be used with the present invention. Since details of the actual pumping mechanism used play no role in the present invention, they are not separately shown in the drawing figures nor further discussed. It is sufficient that each channel 12, 14 has a cassette pump 20 for separately administering a fluid to the patient. More importantly in the present invention is the fact that operation of the cassette pumps in each of the channels is controlled by control device 10, which operates in different modes, as selected by a user (e.g., a patient care provider).

Fluid channel 18, which is also controlled by control device 10, infuses hydration fluid from a fluid container 24 into the patient through tubing 26. Fluid channel 18 may include a conventional volumetric pump.

Each of the channels 12, 14 and the fluid channel 18 is controlled through electrical signals conveyed through an input/output (I/O) card 28. I/O card 28 is electrically connected to the channels 12, 14 and fluid channel 18 so that control signals can be sent to the pump in each channel and so that data signals can be received from the channels. The signals received from the channels indicate alarm conditions, sensor conditions, and the actual rate or amount of drug being delivered to a patient through the channels. These signals pass through I/O card 28 and through a data bus 30 into a processor 32. Processor 32 can be a single board computer which includes a conventional microprocessor or central processing unit (CPU). Also included with processor 32 and coupled to the CPU are both random access memory (RAM) and read only memory (ROM), along with other conventional integrated circuits used on a single board computer as are well known to those of ordinary skill in the art. Single board computers suitable for use in the present invention are available from many different sources.

Processor 32 is coupled through data bus 30 to a graphics display adapter 34. In one embodiment, this graphics display adapter is a conventional video graphics adapter (VGA), of the type commonly used in personal computers. The graphics display adapter is coupled to an electroluminescent (EL) display panel 36 on which instructions and data are presented to a user in both textual and graphic format. In addition, a touch screen 38 is coupled to I/O card 28 for accepting input from a user. The input is converted into signals conveyed on data bus 30 to processor 32. Additional information is presented to the user and selection and input of various parameters is provided on a fluid channel control and indicator panel 40, which is also coupled to processor 32 via I/O card 28 and data bus 30.

A random events generator 39 is also coupled to I/O card 28 for generating a signal which directs a drug or placebo delivery event. The signal is conveyed on data bus 30 to processor 32, which subsequently signals the appropriate pump 20 for execution of the randomly selected delivery event. As noted infra, the type of delivery event can be stored in memory and used to modify subsequent delivery events (so that no more than a predetermined number of sequential placebo delivery events can occur).

Fluid channel control and indicator panel 40 includes a standard 16-button keypad and a plurality of light emitting diodes (LEDs). As shown in a block 44, user input is applied to control the operation of the drug delivery system by selections made on touch screen 38 and by entry of parameters using the keypad. The user input determines the mode of the control device 10. Two modes of drug delivery are provided, including an automated administration mode in which the drug delivery system is used to administer either a bolus dose or a continuous infusion at a predefined rate, and a self-administration mode whereby controlled delivery is initiated by the patient (discussed infra).

On the touch screen, a user enters the age, weight, gender, and other patient specific parameters or drug parameters (if not already stored in the memory associated with processor 32). Parameters which can effect the amount of drug or placebo delivered include, without limitation, total drug administered over a predetermined period of time (e.g., 24 hours), maximum drug dosage per delivery event, whether partial drug delivery is to be utilized and, if so, at what level (e.g., 50% maximum), partial or continuous reinforcement schedule (from zero to 100 percent), frequency of administration (for automated delivery), a maximum number of sequential placebo delivery events which can occur, and a maximum number of drug delivery events which occur without a placebo delivery event.

The user can also selectively determine the information that is displayed on EL display 36 for any drug administered during a patient case, including the partial reinforcement schedule or current drug administered within the last 24 hours, etc. In addition, the user input can selectively determine whether the type of delivery event is to be determined as a purely or semi-random event.

Depending on whether a self-administration mode has been selected, the control device may also include a remote control device 42, which is coupled to the processor 32 via I/O card 28. The remote control device can be either a hard wired or a wireless device. The remote control device sends a signal which is routed through the I/O card to processor 32, in response to which the processor 32 signals pump 20 to initiate a delivery event (discussed infra). If a wireless remote device is used, then a signal detector is also provide for receiving the signal from the remote device and transmitting the signal through I/O card to the processor.

If desired, to load a control program (i.e., for automated modes) into the memory of processor 32, control device 10 includes a 3 ½ inch floppy drive 48. A floppy disk 50 can be inserted into drive 48 to download program files or data, or to receive patient history data for archival storage. The ROM accompanying processor 32 is of the electrically erasable programmable read only memory (EEPROM) type so that drug parameter data can be downloaded from a floppy disk and stored therein. For example, depending on the type of drug being administered, it is possible to load into the memory maximal dosages which cannot be exceeded for a particular drug (i.e., to prevent patient overdose).

The specific drug that is being administered by one of the drug channels could be identified with an entry by the user on the keypad or on the touch screen of the user interface. However, to simplify identification of the drugs being infused by the drug delivery system, a bar code reader 46 is preferably used to scan a drug identification bar code that is affixed to each of the drug vials. Bar code reader 46 may include a fixed scanner that is positioned adjacent each drug or placebo vial 22', or alternatively, a hand-held wand that includes an optical scanner, which is moved to the drug or placebo vial to read its bar code. The ROM accompanying processor 32 stores a table listing specific drugs commonly delivered to a patient by the drug delivery system so that once the bar code on a drug vial has been scanned, processor 32 can determine whether the drug has been recognized as one of those for which data are stored. If not, the user can be prompted with a message on EL display 36 to re-scan the bar code or to indicate that the drug being administered is not among those stored in memory. If drug information is not previously stored in memory, then a user can enter relevant drug data on the touch screen or key pad.

A serial interface 54 can be electrically coupled to processor 32, enabling the host controller to be connected to an external computer, perhaps at a remote site, through a data link 52. Data link 52 can convey data bidirectionally between the external computer and processor 32, enabling, for example, the drug delivery history for a patient to be downloaded to the external computer. A parallel port 58 is also provided in one embodiment to convey output to a printer 56 that is coupled to the parallel port. This output can include a patient drug infusion history showing (selectively in graphical or textual format) the drug or placebo delivery events over a course of time and the interval between such delivery events (for self-administration).

Control device 10 is supplied electrical power from a generally conventional system power supply with a battery backup 60. Although not separately shown, each of the components of the drag delivery system, including those components on control device 10, are connected to the system power supply. In the event that AC line power is disconnected, the battery backup provided with the supply will continue to operate the control device and drug delivery system for an extended period of time.

In controlling each of the channels, the control device 10 produces command signals that are transmitted to a pump (specifically, a processor which controls operation of that pump) within the appropriate channel 12, 14. For example, when control device 10 causes drug channel 12 to begin infusing a drug, the pump processor responds to the command signal from the control device by transmitting a signal that causes motors to be activated, infusing the drug at the nominal rate commanded by the control device. In addition, each channel includes a plurality of sensors that monitor the operation of the cassette pump, producing data signals and alarm signals that are transmitted back to the internal communications block within the control device. Many such signals are important for safe operation of the drug delivery system; however, they have little relationship to the present invention.

In use, a care provider will typically insert appropriate containers into receptacles of the appropriate cassette pumps and install the cassette pumps into the housing of the drug delivery system. As noted previously, the drug can be identified by scanning the barcode on a drug container prior to its installation. After installing the appropriate containers into the drug delivery system, the care provider will then connect a fluid supply line of the patient to an outlet of the drug delivery system. The drug delivery system, specifically the control device thereof, will also be programmed as described below.

Figure 2:
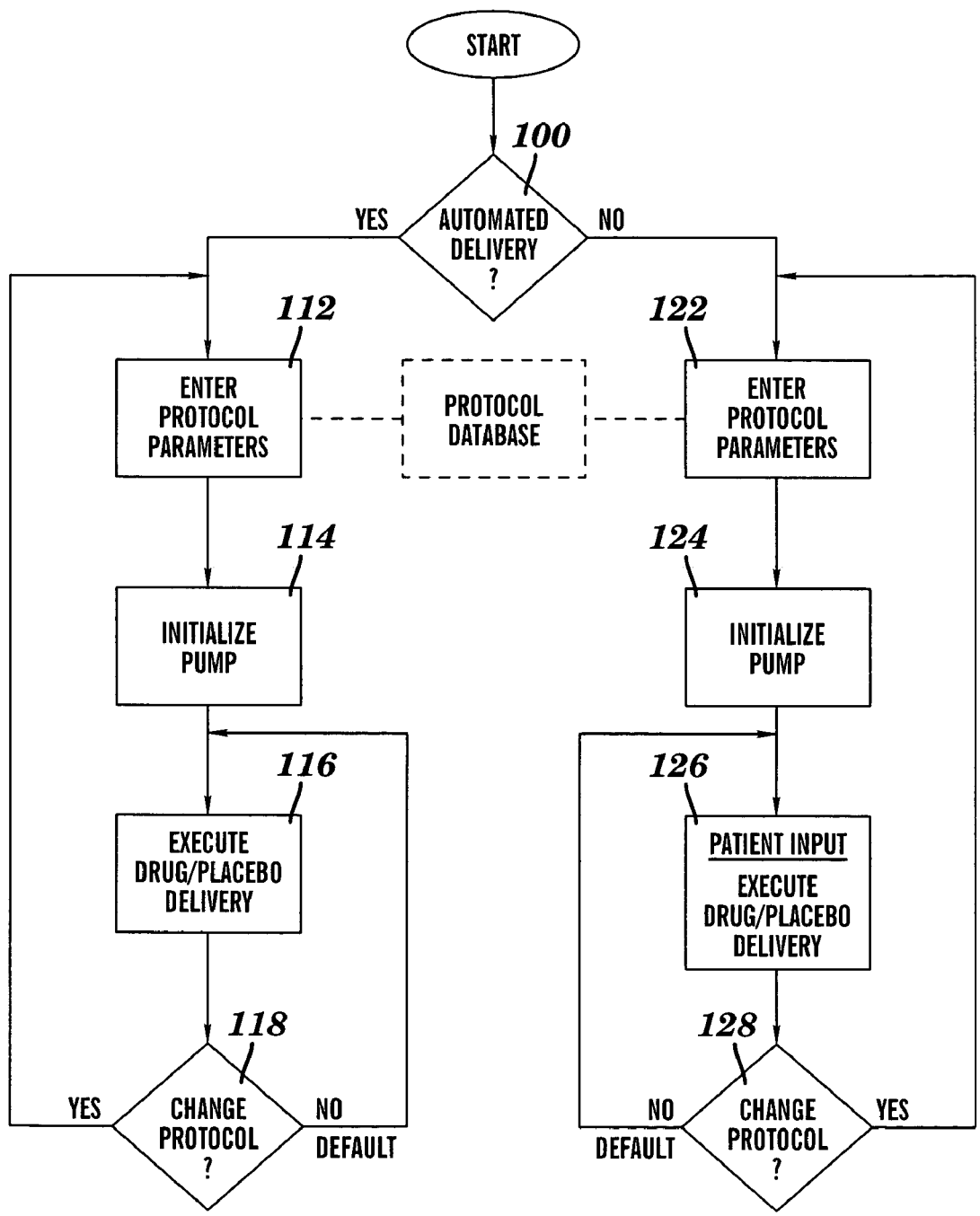
FIG. 2 is a schematic diagram illustrating operation of the logic control device which regulates operation of the one or more pumps delivering either drug, placebo, or both to a patient.

Turning now to FIG. 2, a block diagram shows the relationship between the user input to the system and the control of drug and placebo delivery events by control device 10. Upon starting the drug delivery system, a user is first prompted to select the mode of operation (automated or self-regulated) at decision block 100.

If an automated mode is selected, then the user will be prompted at block 112 to enter parameters which are stored in memory, specifically a protocol database within the memory, for the particulars of automated administration. These parameters are of the type disclosed above. Once all parameters have been entered into the control device 10, the pump is initialized at block 114 and the control device 10 executes at block 116 a set of program instructions that determine a partial reinforcement schedule for drug administration. Following execution of the protocol, a user will be afforded an opportunity to modify the protocol at decision block 118. However, where no input is received, i.e., within a fixed time period, the program automatically repeats itself.

For example, a caregiver can enter (through the user interface provided by the keypad and display) the maximum dosage of the drug during a predetermined period of time (e.g., 24 hour period), the frequency of delivery events (e.g., hourly, every 2 hours, 4 times daily, etc.), as well as desired partial reinforcement schedule. Where a 75 percent partial reinforcement schedule is selected, the patient will automatically receive a placebo bolus on one of every four delivery events. Thus, having received an unconditioned stimulus (drug delivery) along with a conditioned stimulus (sound or lights on the drug delivery system) for three delivery events, the patient will receive only the conditioned stimulus at the time of the placebo delivery event.

Where sub-maximal drug administration is provided (e.g., 50 percent of the programmed maximum dosage), the user can elect for sub-maximal delivery during the automated delivery mode. These sub-maximal delivery events allow drug titer to be reduced in the customary manner, i.e., by reducing the concentration of drug while still providing the patient with a sub-maximal unconditioned stimulus.

If a self-administration mode is selected, then the user will be prompted at block 122 to enter parameters which are stored in memory, specifically a protocol database within the memory, for the particulars of patient-initiated administration. These parameters are of the type disclosed above. Once all parameters have been entered into the control device 10, the pump is initialized at block 124 and the control device 10 executes a set of program instructions that determine a partial reinforcement schedule for drug administration at block 126 upon patient-initiated signaling via remote device 42. Following execution of the protocol, a user will be afforded an opportunity to modify the protocol at decision block 128. However, where no input is received, i.e., within a fixed time period, the program automatically repeats itself.

For example, a caregiver can enter (through the user interface provided by the keypad and display) the maximum dosage of the drug during a predetermined period of time (e.g., 24 hour period), as well as desired partial reinforcement schedule, and, if desired, the maximum number of placebo events which can occur without an intervening drug delivery event as well as the maximum number of drug delivery events which can occur without an intervening placebo delivery event. Where a 75 percent partial reinforcement schedule is selected, each delivery event has a 75 percent chance of being a drug delivery event and only a 25 percent chance of being a placebo delivery event. Each event is randomly selected, independent of all other events, unless a parameter has been entered for regulating the number of placebo events which can occur without an intervening drug delivery event. Thus, no pattern will develop for the occurrence of an unconditioned stimulus (drug delivery along with conditioned stimulus) versus the occurrence of a conditioned stimulus alone.

Regardless of the embodiment of the invention and the mode selected for the administration of the placebo and drug, the mere presence of placebo delivery event, either in whole or in part, in combination with a conditioned stimulus can minimize total drug administration while providing effective pharmacotherapeutic treatments.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A control device for a drug delivery system equipped to deliver at least two fluids, an effective dose of a drug in fluid form and either a placebo or an ineffective dose of the drug in fluid form, the control device comprising:
    a processor that is controlled in accordance with a set of program instructions that determine a partial reinforcement schedule for drug administration;
    a memory, coupled to the processor, said memory storing the set of program instructions and a set of parameters for the partial reinforcement schedule; and
    a user interface, coupled to the processor, said user interface enabling a user to input at least some of the set of parameters used by the partial reinforcement schedule;
    wherein the processor, in executing the set of program instructions, delivers the effective dose of the drug, the placebo or ineffective dose of the drug, or both, to a patient according to the partial reinforcement schedule.

2. The control device according to claim 1 further comprising:
    a display, coupled to the processor, on which are displayed the set of parameters or status of the partial reinforcement schedule.

3. The control device according to claim 1 wherein the processor is controlled by the set of program instructions and the set of parameters to administer the effective dose of the drug, the placebo or ineffective dose of the drug, or both, whereby each delivery event is randomly selected according to a probability determined by the set of parameters.

4. The control device according to claim 3 further comprising:
    a random events generator, coupled to the processor, said random events generator signaling to the processor whether the effective dose of the drug, the placebo or ineffective dose of the drug, or both, are to be delivered to the patient on a particular delivery event.

5. The control device according to claim 1 further comprising:
    a switch, coupled to the processor, enabling the user to select between a manual mode and an automated mode for controlling the timing of processor execution of the set of program instructions.

6. The control device according to claim 5 further comprising:
    a wired or wireless remote device, coupled to the processor, for signaling to processor when to execute the set of program instructions.

7. A drug delivery system comprising:
    a housing;
    a first receptacle in said housing which is adapted to receive a first container comprising an effective dose of a drug in fluid form;
    a second receptacle in said housing which is adapted to receive a second container comprising a placebo or an ineffective dose of the drug in fluid form;
    an outlet which, upon introduction of the first and second containers into the first and second receptacles, respectively, is in communication therewith;
    one or more pumps which act upon the first and second containers; and
    a control device which controls operation of the one or more pumps to deliver the effective dose of the drug or the placebo or ineffective dose of the drug from the outlet according to a partial reinforcement schedule, whereby the placebo or ineffective dose of the drug is delivered in whole or in part during one or more delivery events.

8. The drug delivery system according to claim 7, wherein the control device comprises:
    a processor that is controlled in accordance with a set of program instructions that determine the partial reinforcement schedule for drug administration; and
    a memory, coupled to the processor, said memory storing the set of program instructions and a set of parameters for the partial reinforcement schedule.

9. The drug delivery system according to claim 8, wherein the control device further comprises:
    a user interface, coupled to the processor, said user interface enabling a user to input at least some of the set of parameters used by the partial reinforcement schedule.

10. The drug delivery system according to claim 8 wherein the control device further comprises:
    a display, coupled to the processor, on which are displayed the set of parameters or status of the partial reinforcement schedule.

11. The drug delivery system according to claim 8 wherein the control device further comprises:
    a random events generator, coupled to the processor, said random events generator signaling to the processor whether the effective dose of the drug, the placebo or ineffective dose of the drug, or both, are to be delivered to the patient on a particular delivery event.

12. The drug delivery system according to claim 8 further comprising:
a switch, coupled to the processor, enabling the user to select between a manual mode and an automated mode for controlling the timing of processor execution of the set of program instructions.

13. The drug delivery system according to claim 7 wherein the one or more pumps comprise a first pump which acts upon the first container and a second pump which acts upon the second container.

14. The drug delivery system according to claim 7 further comprising:
a wired or wireless remote device, coupled to the processor, for signaling to processor when to execute the set of program instructions.

15. A method of automatically modulating drug/placebo delivery to a patient comprising:
connecting a fluid supply line of a patient to an outlet of a drug delivery system according to claim 7, with the drug delivery system provided with a first container comprising an effective dose of a drug in fluid form and a second container comprising either a placebo or an ineffective dose of the drug in fluid form;
programming the control device with a drug dosage rate for a predetermined period of time; and
operating the drug delivery system for the predetermined period of time, whereby drug delivery during the predetermined period of time is modulated by delivery of the placebo or the ineffective dose of the drug, either in whole or in part, during one or more delivery events occurring during the predetermined period of time.

16. The method according to claim 15 wherein said programming further comprises programming the control device with a partial reinforcement schedule for delivery of the placebo or the ineffective dose of the drug, either in whole or in part, during the one or more delivery events.

17. The method according to claim 15 wherein the second container comprises a placebo.

18. A method of modulating patient self-delivery of a drug comprising:
connecting a fluid supply line of a patient to an outlet of a drug delivery system according to claim 7, with the drug delivery system provided with a first container comprising an effective dose of a drug in fluid form and a second container comprising a placebo or an ineffective dose of the drug in fluid form;
programming the control device with a drug dosage rate; and
operating the drug delivery system, whereby drug delivery is modulated by delivery of the placebo or the ineffective dose of the drug, either in whole or in part, during one or more patient-regulated delivery events.

19. The method according to claim 18 wherein said programming further comprises programming the control device with a partial reinforcement schedule for delivery of the placebo or the ineffective dose of the drug, either in whole or in part, during the one or more patient-regulated delivery events.

20. The method according to claim 18 wherein the second container comprises a placebo.

\* \* \* \* \*